United States Patent
Aliperti et al.

(10) Patent No.: US 7,056,319 B2
(45) Date of Patent: Jun. 6, 2006

(54) SPHINCTEROTOME AND MANOMETRY CATHETER

(75) Inventors: Giuseppe Aliperti, St. Louis, MO (US); Jason M. Gaskill, Wright City, MO (US)

(73) Assignee: Wilson-Cook Medical, Inc., Winston-Salem, NC (US)

( * ) Notice: Subject to any disclaimer, the term of this patent is extended or adjusted under 35 U.S.C. 154(b) by 32 days.

(21) Appl. No.: 10/309,681

(22) Filed: Dec. 3, 2002

(65) Prior Publication Data
US 2003/0130679 A1    Jul. 10, 2003

Related U.S. Application Data

(60) Provisional application No. 60/338,727, filed on Dec. 4, 2001.

(51) Int. Cl.
A61B 18/14    (2006.01)
A61B 17/32    (2006.01)

(52) U.S. Cl. .......................... 606/41; 606/45; 606/47; 606/170; 600/561

(58) Field of Classification Search .................. 606/47, 606/170, 41, 45; 600/561, 587
See application file for complete search history.

(56) References Cited

U.S. PATENT DOCUMENTS

| 4,809,710 | A | 3/1989 | Williamson |
| 5,339,799 | A | 8/1994 | Kami et al. |
| 5,810,807 | A | 9/1998 | Ganz et al. |
| 6,113,490 | A | 9/2000 | Fischer et al. |
| 6,533,782 | B1 * | 3/2003 | Howell et al. .................. 606/47 |
| 6,676,659 | B1 * | 1/2004 | Hutchins et al. ............... 606/47 |
| 6,692,490 | B1 * | 2/2004 | Edwards ........................ 606/41 |
| 2002/0072745 | A1 * | 6/2002 | Truckai et al. .................. 606/47 |

FOREIGN PATENT DOCUMENTS

| WO | WO 01/87399 A2 | 11/2001 |
| WO | WO 01/89624 A1 | 11/2001 |

* cited by examiner

*Primary Examiner*—Lee S. Cohen
(74) *Attorney, Agent, or Firm*—Brinks Hofer Gilson & Lione

(57) ABSTRACT

A catheter for diagnosis of sphincter motility by measuring pressure exerted by the sphincter and, when necessary, ablating the sphincter immediately after diagnosis of a dysfunction. The catheter is in the form of an elongate sheath that has a proximal end, a distal end, and a longitudinal portion therebetween, with a manometry data collecting portion and a sphincterotome portion located at the distal end, and a handle assembly located at the proximal end. Embodiments are shown wherein the distal end can be aimed in a direction that facilitates cannulating the sphincter by moving the handle assembly. The catheter is used by maneuvering the distal end of the catheter into a sphincter. The manometry data collecting portion is first aligned with the sphincter and pressure measurements are taken. If it is determined that the sphincter is dysfunctional, the sphincterotome portion is aligned with and used to ablate the dysfunctional sphincter.

27 Claims, 5 Drawing Sheets

US 7,056,319 B2

SPHINCTEROTOME AND MANOMETRY CATHETER

This application claims priority to U.S. Provisional Application Ser. No. 60/338,727, filed Dec. 4, 2001.

TECHNICAL FIELD

This invention relates to medical devices, more particularly to catheters for diagnosis and ablation of dysfunctional sphincters.

BACKGROUND OF THE INVENTION

The sphincter of Oddi is located at the confluence of the bile duct, the pancreatic duct, and the duodenum, where it regulates the flow of bile and pancreatic juices into the small intestine, typically following the ingestion of a meal. Both biliary and pancreatic sphincters are part of the sphincter of Oddi, which is subject to a medical condition known as Sphincter of Oddi Dysfunction (SOD), a motility disorder. SOD can manifest itself as various problems within the bile or pancreatic ducts, such as formation of gallstones that obstruct the biliary duct, pancreatitis resulting from retrograde bile flow into the pancreatic duct, or post-cholecystectomy pain. Sphincter of Oddi Dysfunction has been found to be a leading cause of recurrent pancreatitis. Diagnosis of SOD can be performed by an endoscopist during a Endoscopic Retrograde Cholangiopancreatography (ERCP) by assessing the basal sphincter pressure using a manometry catheter, also called a motility catheter. The catheter, which is designed to be situated within sphincter of Oddi, includes one or more distal ports that infuse saline against the walls of the sphincter. The pressure exerted by the muscles of the sphincter is measured and used to assess the tone of sphincter and help determine if SOD is present. One example of a SOD manometry catheter is the Lehman Sphincter of Oddi Manometry Catheter (Wilson-Cook Medical, Winston-Salem, N.C.). It is a three-lumen catheter with two manometry ports located about the distal end. The two ports communicate with two luer connectors which attach to transducer of a separate recording system for measuring the resistance applied by the sphincter to the saline being infused through the ports by an infusion pump which also has been attached to the manometry catheter. After flushing the wire guide lumen, the catheter is fed over the wire guide pre-positioned in the bile duct and then into the endoscope accessory channel. The manometry catheter is then maneuvered under endoscopy into the cannulated SOD and a series of pressure readings are made to access the condition of the sphincter. A basal tone of more than 40 mm Hg is an indicator that the sphincter cannot effectively regulate bile flow and/or pass smaller stones into the duodenum.

Typically, a hypertensive SOD is treated by ablation of the sphincter muscles, a procedure called a sphincterotomy, using a second, specialized catheter known as a sphincterotome. A biliary sphincterotome is an endoscopic catheter that includes a wire, typically braided or monofilament stainless steel, that extends from the distal end of the catheter or exits the catheter for only a portion of its length. The wire is connected to a electrosurgical generator that delivers current that allows the wire to ablate tissue with which it comes into contact. A sphincterotomy is often selected as the desired treatment after a manometry catheter has been used to establish that the sphincter is hypertensive. The manometry catheter must first be removed from the scope accessory channel, which is only large enough to accommodate a single device. The sphincterotome is then fed over the wire guide, if used, which remains in the bile duct. After the physician has maneuvered the sphincterotome into the papilla, current is applied to the cutting wire and the sphincter muscles are ablated, thereby creating a larger opening for the drainage of bile and/or passage of stones.

Depending on the symptoms displayed by the patients, the likelihood of a sphincterotomy being performed can be rather high, once the physician has made the decision that the basal tone of the sphincter should be measured via a manometry catheter. Therefore, in a large number of patients, a sphincterotome will be required to be introduced through the endoscope to the site to replace the manometry catheter. What is needed is a way to more efficiently treat SOD by eliminating the need to replace devices once a confirmation of sphincter hypertension has been made. Ideally, such a solution should reduce the overall duration of the combined diagnostic and therapeutic procedures while including the full ability to perform each. Furthermore, such a device should reduce the risks associated with introducing a second device and be cost effective over a reasonable number of procedures, taking into account that there is a significant percentage of SOD studies that do not result in a sphincterotomy being performed.

SUMMARY OF THE INVENTION

The foregoing problems are solved and a technical advance is achieved in an illustrative sheath or catheter that includes both side ports and dedicated passageways configured for supplying infusate used to acquire manometry data within the sphincter of Oddi, while also including a cutting wire (or needle knife) for performing a subsequent sphincterotomy if indicated by analysis of the manometry data. The combinational manometry catheter and sphincterotome eliminates the need for two separate devices being required, since one device will perform the function of both. Although it is likely that such a device would cost more than a sphincterotome or a manometry catheter alone, it certainly would be less expensive than the combined cost of the two devices. Furthermore, the primary cost advantage is in the reduction of the procedure time by being able to immediately perform a sphincterotomy without having to first remove the manometry catheter. The obvious clinical benefits for the patient include not having to access the papilla and duct a second time and shortening the total time that the devices remain within the patient. Over the course of multiple procedures, the cost and clinical benefits of a dual-function device clearly outweigh any additional cost that the sphincterotome-specific components add in those instances when a sphincterotomy proves unnecessary. In the illustrative embodiment, the deflectable aspect of the sphincterotome portion adds a useful feature for negotiating the manometry data collecting portion into the papilla, especially being that manometry catheters typically lack such a capability.

The present invention includes an elongate sheath portion having a plurality of passageways that include at least one for infusion of fluids and subsequent measurement of the result fluid pressure, and one to house a cutting wire adapted to ablate adjacent tissue when a current is supplied. Optionally, a lumen is included to accommodate a standard wire guide and/or the infusion of fluids, such as saline or contrast agents. A proximal assembly comprises the proximal portion of the catheter assembly, including a handle portion that is operatively connected to the sheath portion, the handle portion preferably including a electrical connector for connecting to an electrosurgical generator/electrocautery unit for supplying current to the cutting wire; a wire guide port, such as a side arm adaptor; and one or more connectors to attach to a data collection system that includes the necessary components for data acquisition. Typically included in the data collection system is an infusion pump for delivering fluid to the manometric recording ports, one or more transducers for reading the pressure of the individual columns of infusate as they encounter the resistance supplied by the sphincter muscles, and a recording unit, such as a computer and appropriate commercially available function testing software, to analyze and display the manometric data, allowing the physician to access the condition of the sphincter.

In one preferred embodiment of the invention, the sheath portion comprises a four-lumen polytetrafluoroethylene (PTFE) catheter with three smaller lumens or passageways to accommodate two infusion ports and the sphincterotome cutting wire; and a lumen sized to accommodate a standard wire guide used in the procedure. Some physicians do not use a wire guide to cannulate the papilla as part of the procedure. Therefore, the larger wire guide passageway can be considered optional, leaving a three-lumen catheter. The cutting wire exits the tubing along the distal portion of the sheath for a distance sufficient to allow ablation of the sphincter or papilla when properly positioned. The cutting wire reenters the tubing distally, where it terminates and is affixed to the catheter. The cutting wire can be advanced and retracted longitudinally independent of the catheter portion via the sliding handle. This allows the distal portion of the catheter portion to be deflected in one direction to assist in accessing the papilla. The bowing of the distal portion shortens the cutting portion of the wire and can produce an advantageous configuration for ablation. The two infusion passageways terminate along the distal portion at the respective infusion port of each, which are located approximately 90° with respect to one another. Plugs such as stainless steel wire pieces are placed within each passageway just distal to the port, thereby forcing the fluid to exit at the manometry port. The distal portion of the catheter includes a series of markings that are used as a visual indicator of how far to withdraw the catheter from the papilla of Vater to make a series of successive readings within the sphincter.

In another preferred embodiment of the present invention, the catheter includes five passageways. One passageway is typically larger for accommodating a standard wire guide. The three smaller passageways are adapted for fluid transport, with the fourth reserved for the cutting wire. Either each of the three are provided for infusion and manometric data collection, or one of the passageways is adapted for aspiration of fluid supplied by the other two to help prevent overfilling of the bile or pancreatic ducts and the associated complications that could result. The aspiration port and passageway can also be present in a sheath with fewer than five passageways, with either the wire guide passageway or one of two infusion passageways being eliminated.

BRIEF DESCRIPTION OF THE DRAWINGS

Embodiments of the present invention will now be described by way of example with reference to the accompanying drawings, in which.

Figure 8:
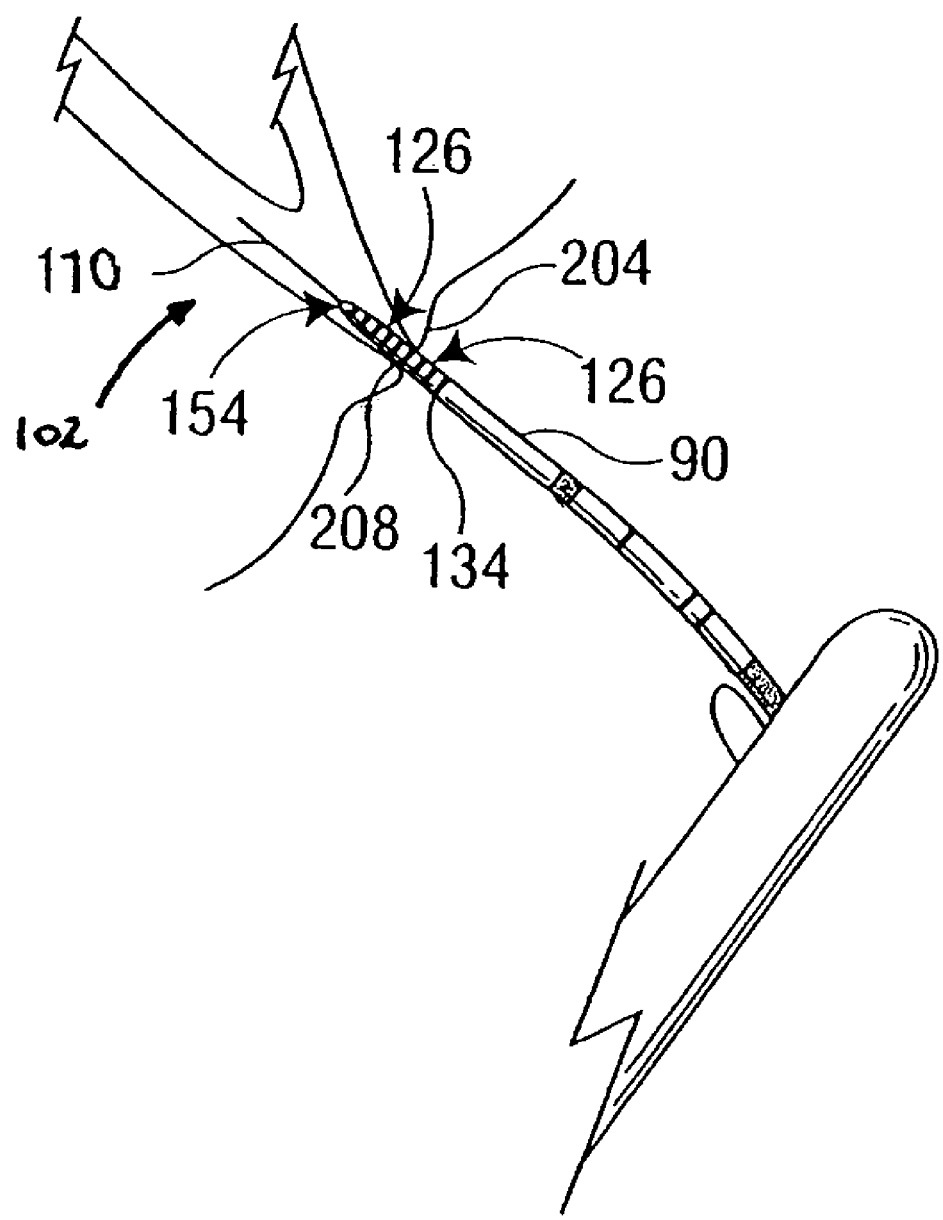
FIG. 8 depicts a side view of an illustrative embodiment of the present invention.

As will become apparent to one of ordinary skill in the art, the cutting wire used in a sphincterotome can be provided in a variety of cutting configurations. For example, as illustrated in FIG. 8, sphincterotome portion 102 includes a cutting wire 110 that projects distally from sheath 90. In this sphincterotome configuration, cutting wire 110 can be used as a needle knife or an electrosurgical cutter.

DETAILED DESCRIPTION OF THE INVENTION

Figure 1:
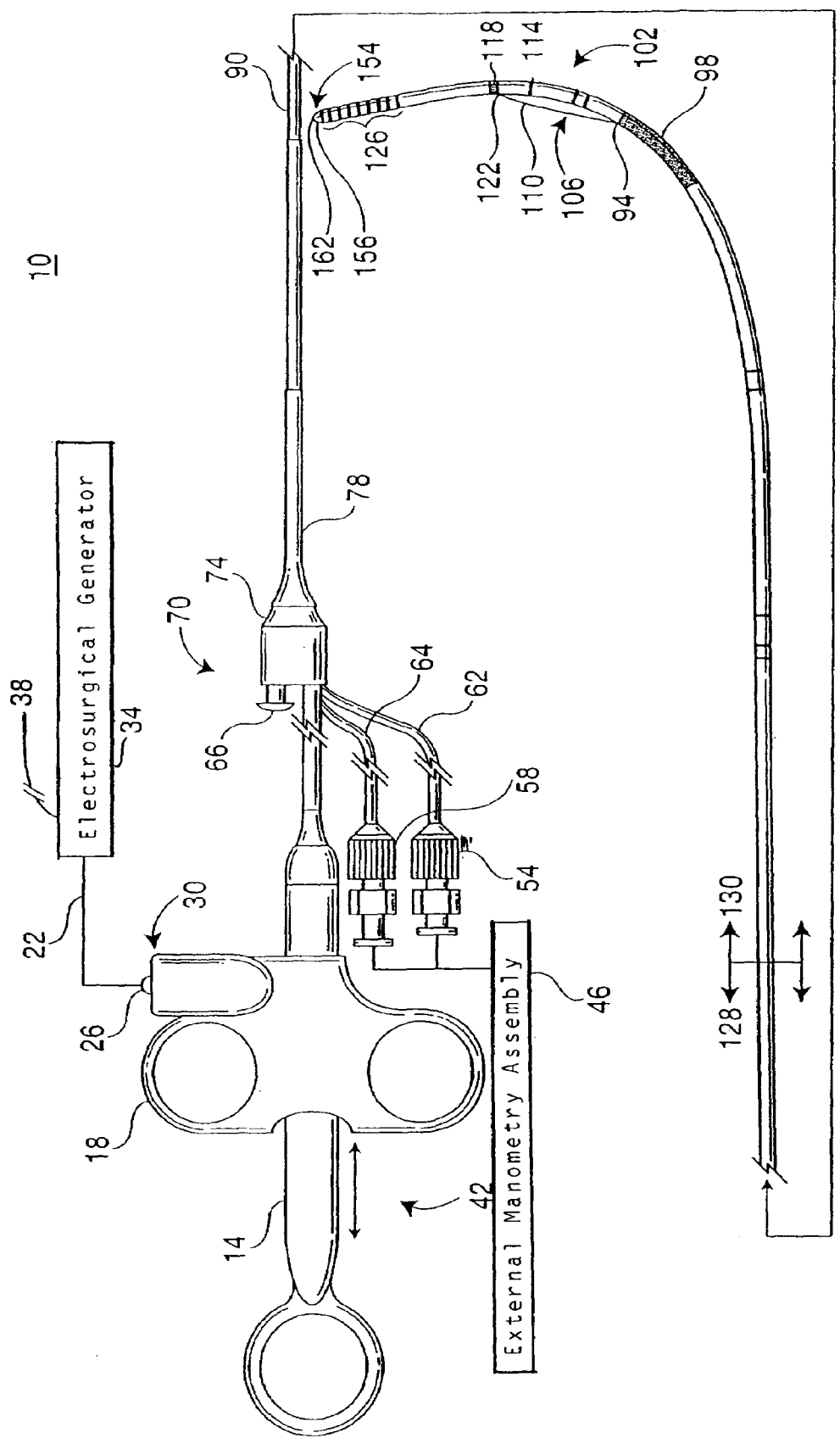
FIG. 1 depicts a side view of an illustrative embodiment of the present invention.
Figure 2:
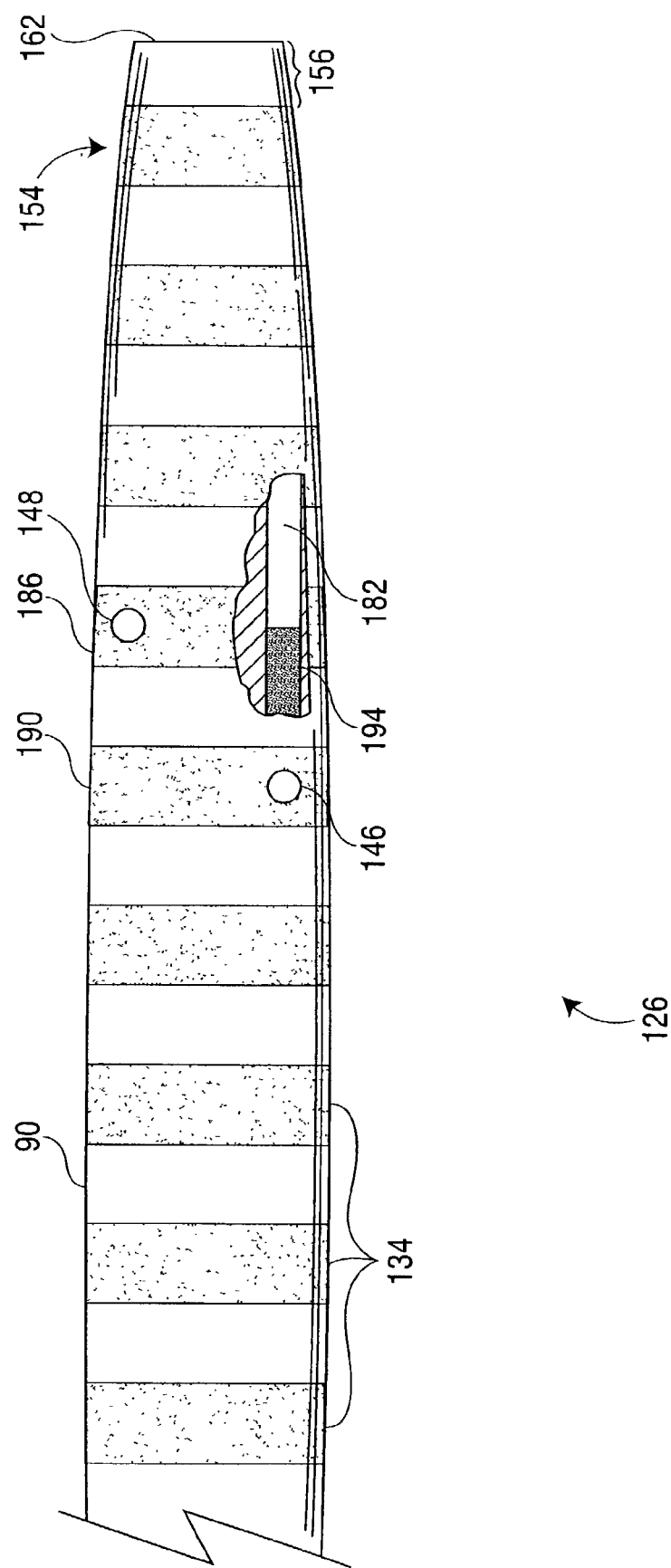
FIG. 2 depicts an enlarged, partially sectioned bottom view of the manometry data collecting portion of the embodiment of FIG. 1.
Figure 3:
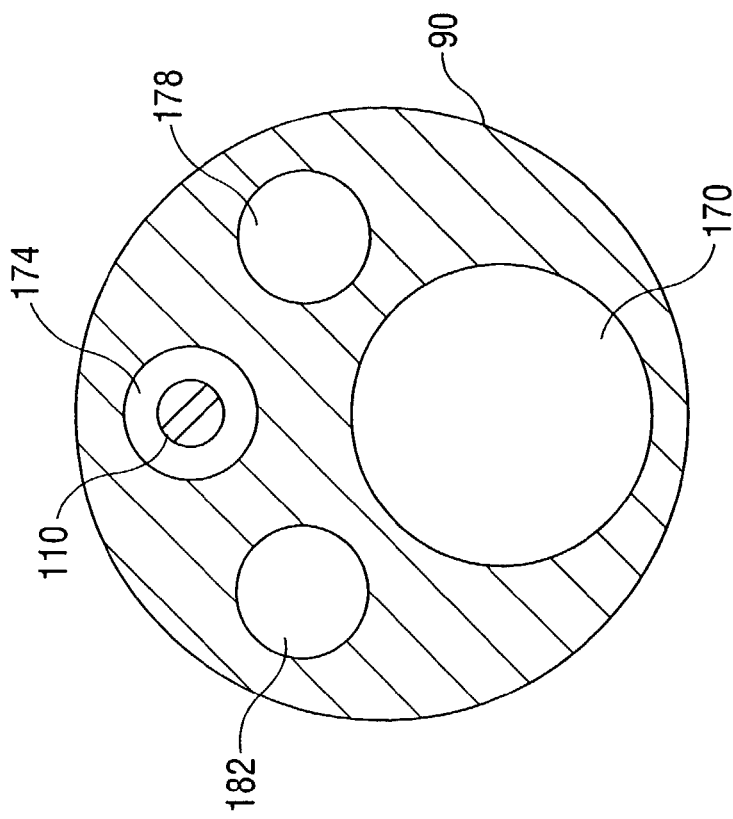
FIG. 3 depicts a cross-sectional view taken along line 3—3 of FIG. 1.

Referring now to FIGS. 1–3, a first embodiment of the catheter assembly 10 of the present invention is depicted, comprising a sheath portion 90, including a manometry data-collecting portion 126 and a sphincterotome portion 106, and a proximal assembly 70. In the illustrative embodiment intended for biliary use, the overall length of the sheath 90 and proximal assembly 70 is approximately 215 cm, the proximal assembly 70 comprising about 30–35 cm of that length. The sheath portion 90 of the illustrative embodiment comprises a four-lumen, polytetrafluorethylene (PTFE) catheter. PTFE is a preferred material because of its lubricity and pushability within the scope; however, one skilled in the catheter arts would recognize that other polymers may be used. The OUTSIDE DIAMETER ("OD") of the sheath 90 tubing is approximately 0.094 mm to allow the sheath 90 to pass within the accessory channel of a standard endoscope, such as a duodescope. The distal portion 130 of the catheter advantageously includes a taper 154 that measures approximately 4.5–5.0 Fr at the distal end 156 of the catheter. The distal end 156 includes an opening to a passageway 162 to accommodate a standard wire guide used in a biliary procedure, such as a 0.35" TRACER® Wire Guide (Wilson-Cook Medical, Inc.). In the illustrative embodiment the wire guide passageway 162, depicted in FIG. 3, is approximately 0.041 mm. The remaining three passageways 174, 178, 182, which do not functionally extend to the distal end 156, are approximately 0.022 mm, with two passageways 178, 182 being for the infusion of fluid (typically saline) used for manometric measurement. The third passageway 174 is adapted for carrying the cutting wire 110 that extends from proximal assembly 70 to the sphincterotome portion 102 of the distal portion 130, where it exits the passageway 174 at a proximal opening 94 for approximately 20–30 mm, forming the cutting portion 106 of the sphincterotome, before reentering the sheath at a distal opening 122, where it terminates. Bands 98, 118 such as tantalum bands, mark the exit and reentry points 94, 122 of the cutting wire 110, respectively. The distal band 118 further serves to secure and anchor the cutting wire 110 as it reenters the passageway 174. Standard depth markings 114 are provided as a visual guide to aid in ablation, these being located between the distal and proximal markings 98, 118. For the purposes of this application, the sphincterotome portion 102 is defined as that portion of the catheter assembly 10 that is adapted for cutting or ablating a sphincter or papilla, via electrosurgical or other means, for the purposes of facilitating the passage of materials therethrough. While the illustrative embodiment is adapted for biliary use to ablate the sphincter of Oddi, and the papilla of Vater, the present invention would include devices configured for treating other problematic sphincters, e.g., the anal sphincter.

Figure 4:
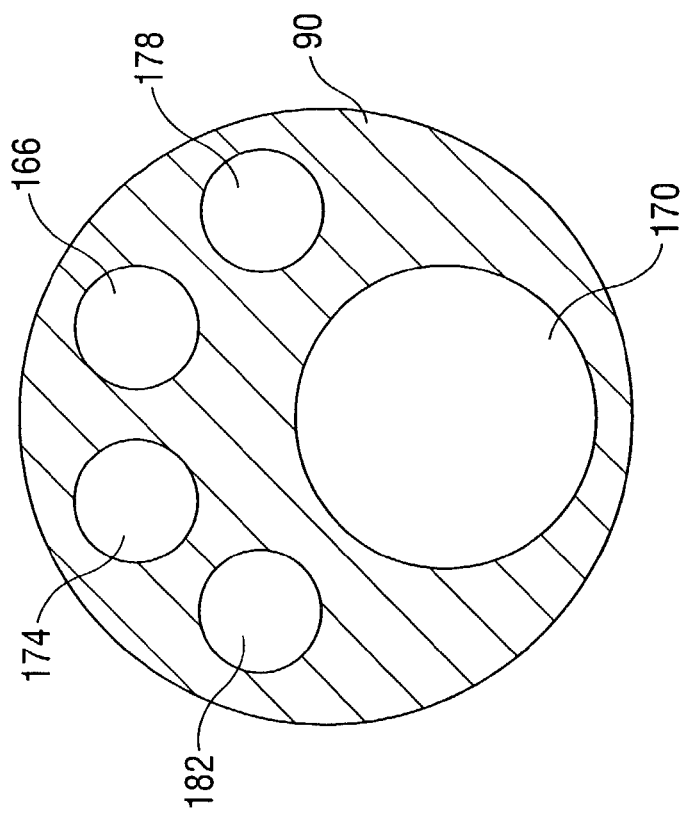
FIG. 4 depicts a cross-sectional view of an alternative embodiment having four passageways.

In another embodiment depicted in FIG. 4, the sheath includes an aspiration lumen 166, such that there are a total of five passageways. The aspiration lumen 166 communicates with a third proximal connector (not illustrated) at the proximal assembly 70 which is connectable to an automatic or manual aspiration apparatus, such as a vacuum pump, syringe, etc. The aspiration apparatus can be used continually or intermittently to aspirate excess infusate delivery from the manometry recording ports 146, 148 to prevent overfilling of the bile and pancreatic ducts.

Referring now to FIGS. 1 and 2, distal to the sphincterotome portion 102 lies the manometry data collecting portion 126 of the catheter assembly 10. The length of the manometry data collecting portion 126 and relationship to the sphincterotome portion 102 can be variable, depending on use and preference. In the illustrative embodiment, there is 35–40 mm of catheter tubing beyond the distal opening 122 where the cutting wire 110 enters the tubing, generally a greater length than would be found in a standard sphincterotome. The manometry data collecting portion of the illustrative embodiment comprises the distal 20–25 mm of the distal portion 130 and includes a series of ten radiopaque marker bands 134, approximately 1 mm in width, located about 2 mm apart. These markings 134 are used as a visual guide to the operator, when viewing through the endoscope, to allow the operator to make notation on the chart when each of the markings correspond to a certain relative position within the duct and sphincter. Generally, the fluid is being infused continually while the catheter is being withdrawn from the sphincter of Oddi. When the first marking becomes visible at the opening of the papilla, the operator can place a mark on the chart to indicate the relative position of the catheter. When the second mark becomes visible, a second mark is made on the chart and so forth until the fourth marking 186 at the distal most manometry recording port 148 is reached. After that port 148 has exited the papilla, there will be rapid drop as the duodenal pressure is then recorded.

The first and second manometry recording ports 146,148 are located on the fifth 190 and fourth 186 marker bands, respectively, counting from the distal end 154. The ports 146, 148 are formed by making a generally circular bore, typically about 0.02" in diameter, through the outer wall of the sheath 90 and into the respective passageways 178, 182. Just distal to each port 146, 148, a plug 194, such as short section of stainless steel wire, is placed within the passageway 178, 182 which lodges within, and blocks the passageway. The plug forces the infusate that is being delivered through the passageway to exit via the port, where it is encountered by tissue that supplies resistance against the column of infusate, thereby resulting in a measurable back pressure that can be detected by a transducer that is in communication with the passageway containing the infusate. One skilled in the art would understand and appreciate the principles of manometry data collection and the necessary configuration of the manometry instrumentation required to obtain an accurate assessment of the compliance of the sphincter of Oddi.

Remote operation of the sphincterotome and manometry functions of the present catheter assembly 10 takes place via the proximal assembly 70, which in the illustrative embodiment of FIG. 1, includes a handle portion 42 that comprises a standard sliding, three-ring handle having a first portion 14 with a single ring to accommodate the operator's thumb and a second portion 18, slidable relative to the first portion 14, that includes a pair of rings, typically to accommodate the index and middle fingers of the operator. In the illustrative handle 42, cutting wire 110 which extends proximally from the sphincterotome portion 102 is attached inside the second, slidable portion 18 to an electrical connector 30 that is adapted such that the external end conveniently forms a male plug 26 that is received by an electrical cord 22 (sometimes called an 'active cord') configured for use with the particular type of sphincterotome, the cord 22 being connectable to a standard electrosurgical generator 34, such as those manufactured by Valleylab, Inc. (Boulder, Colo.). The operator, via the generator 34, controls whether current is applied to the catheter assembly 10, typically using a foot pedal to electrify the cutting wire 110 and ablate tissue coming in contact with the wire. The slidable handle 14 allows tension to be placed on the cutting wire 110 as the handle 14 is retracted, thereby causing the distal portion 130 of the sheath 90 to deflect toward the wire. This permits the distal portion 130, including both the sphincterotome portion 102 and the manometry data collecting portion 126, to be directed with increased accuracy to the target region and better orient with the anatomy.

The portion of the proximal assembly 42 configured for operation of the manometry function of the illustrative catheter assembly 10 comprises a side port assembly 74 by which communication is established with the first, second, and wire guide passageways 174, 178, 182 of the sheath 90. A scive or opening (not shown) is established through the tubing into each of the aforementioned passageways. At the access points to the first and second passageways 178, 182 which communicate with the manometry recording ports 146, 148, tubing 62, 64, such as standard 4.5 Fr O.D. PTFE tubing, is joined at the scive and secured to the sheath. Typically, a well-known technique is used, whereby a short section of cannula (not shown) is inserted into the scive, with the tubing 62, 64 fitted thereover. One or more outer protective sleeves 78, preferably including shrink tubing, are used to help secure and protect the junction of the tubing 62, 64 and sheath 90, as well as the junction of the wire guide port 66 with the wire guide passageway 170. The illustrative wire guide port 66 is configured for attachment of a stopcock for infusing contrast media, saline, or other agents. Optionally, the wire guide port 66 can include a Tuohy-Borst adaptor (possibly in combination with a stopcock) which allows the liquid agent to be injected around a wire guide as it is positioned in the wire guide passageway, such that fluid does not leak from the wire guide port. With regard to the manometry tubing 62, 64 first and second luer or other standard-type connectors 54, 58 are attached to the tubing 62, 64 extending from the junctions with first and second passageways 178, 182, respectively. These connectors, which may be conveniently color coded, are connectable to a suitable external manometry operative assembly 46, which typically includes an infusion pump, such as a Pneumohydraulic Capillary Infusion System available from Arndorfer Medical Specialties, Inc., Greendale, Wis., separate transducers for each recording port 146, 148 and a data recording unit for stationary manometry, such as a unit available from Medtronic Synectics, Shoreview, Minn. The particular components used to measure, analyze, and record manometry data are not regarded as an essential part of the present invention. One skilled in this art area should possess knowledge of available and appropriate substitutions that can be made within an exemplary system for obtaining manometry data. For example, placement of the transducers for measuring pressures within the infusate pathway can be alternatively placed within the distal portion of the sheath. As such, the associated conductor wires would extend through the sheath back to appropriate connectors located about the proximal assembly 70.

Figures 5, 6, 7:
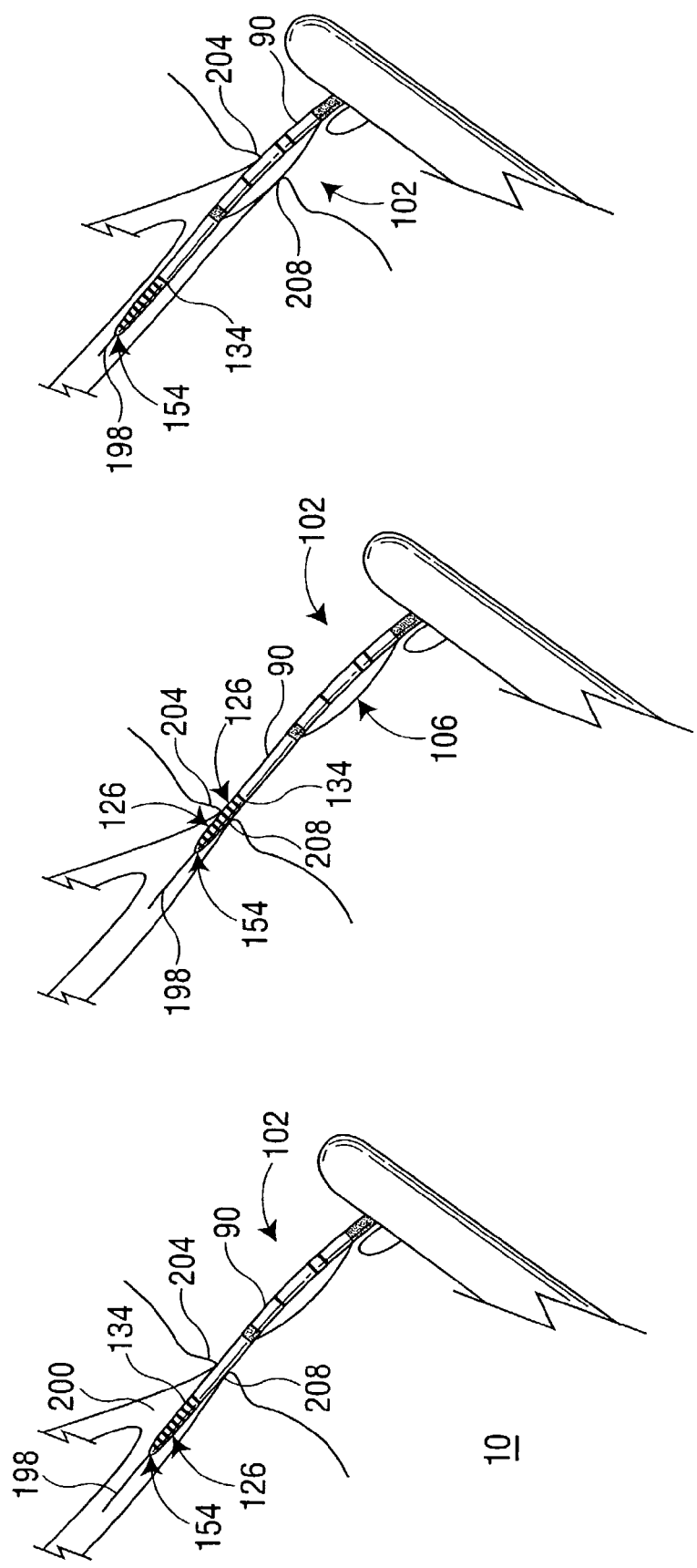
FIGS. 5–7 depict a method of using the embodiment of FIG. 1 to both measure and treat the sphincter of Oddi in a patient.

FIGS. 5–7 depict typical usage of the embodiment of FIG. 1 being used to diagnosis and treat SOD in a patient. FIG. 5 shows the present catheter assembly 10 being introduced into the common bile duct 200 via a standard duodescope, often after an ERCP procedure has already been performed. A standard wire guide 198 is shown extending distally from the sheath 90 which may be used to cannulate the papilla of Vater 204 and common bile duct 200. To obtain the manometry readings within the sphincter of Oddi 208, the distal end 154 of the sheath 90 is introduced through the papilla 204 (by tracking over the pre-existing wire guide 198 in the illustrative example) until the manometry data collecting portion 126 of the sheath 90 is completely within the common bile duct 200 and sphincter of Oddi 208. As shown in FIG. 6, the sheath is then withdrawn while the saline is being constantly infused by the attached pump (not shown). As discussed previously, the markings 134 are used so that the notations can be made on the data chart as particular marks become visible through the endoscope. The readings are used to form a profile of the muscular compliance along the length of the sphincter of Oddi 208. Usually, three or four passes are made with the manometry catheter in order to obtain sufficient data for analysis. The number of passes required is partially determined by the number of manometry recording ports with fewer ports requiring additional passes. The pressure readings measured within the sphincter of Oddi 208 help the physician determine if a sphincterotomy (sometimes called a papillotomy if performed by cutting from outside of the papilla into the sphincter) would be an appropriate treatment for the patient. If so, the sheath 82 is further advanced into the common bile duct 200, as depicted in FIG. 7, until the sphincterotome portion 102 of the sheath 90 is aligned with the sphincter of Oddi 208 with the cutting portion 106 properly oriented to ablate the sphincter 208 and/or papilla 204 and enlarge the opening to the duodenum. The sphincterotomy/papillotomy is performed as it would be with a typical sphincterotome, depending on clinical factors, such as whether the sphincter needs to be pre-cut to allow better access, then the sheath 90 is pulled back into the endoscope and withdrawn from the patient. The described procedure may be varied according to physician preference and the particular needs of the patient. Ablation procedures for other anatomical sites should be based on existing practice and should be already apparent to one skilled in the particular procedure.

Any other undisclosed or incidental details of the construction or composition of the various elements of the disclosed embodiment of the present invention are not believed to be critical to the achievement of the advantages of the present invention, so long as the element possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention. Unless otherwise indicated, all ordinary words and terms used herein shall take their customary meaning as defined in The New Shorter Oxford English Dictionary, 1993 edition. All technical terms shall take on their customary meaning as established by the appropriate technical discipline utilized by those normally skilled in that particular art area. All medical terms shall take their meaning as defined by Stedman's Medical Dictionary, 27th edition.

The invention claimed is:

1. A catheter device for diagnosing a dysfunctional sphincter and ablating the sphincter, comprising:
   an elongate sheath comprising a manometry data collecting portion and a sphincter cutting portion;
   wherein the elongate sheath further comprises:
   a proximal end, a distal end and a longitudinal axis extending therebetween, the distal end comprising the sphincter cutting portion;
   a cutting wire passageway extending along the longitudinal axis from the proximal end to the sphincter cutting portion;
   a cutting wire extending longitudinally through the cutting wire passageway from the proximal end to the sphincter cutting portion, the cutting wire having an exposed portion located alongside the sphincter cutting portion;
   an anchor connecting the cutting wire to the sphincter cutting portion; and
   a handle disposed near the proximal end of the elongate sheath and operatively connected to the cutting wire,
   wherein the cutting wire is adapted for ablating the sphincter.

2. The catheter device of claim 1, wherein the elongate sheath further comprises:
   the distal end further comprising the manometry data collecting portion;
   a manometry passageway extending along the longitudinal axis from the proximal end to the manometry data collecting portion, the manometry passageway terminating at the manometry data collecting portion in an exit port;
   a pressure transducer operatively connected to the manometry passageway; and
   a manometry assembly removably coupled to the manometry passageway at the proximal end, the manometry assembly comprising an infusion pump operatively connected to the manometry passageway, and a data recording unit operatively connected to the pressure transducer,
   wherein a tension of the sphincter is determined by measuring the pressure of a column of fluid infused through the manometry passageway.

3. The catheter device of claim 2 further comprising:
   a guide wire passageway extending along the longitudinal axis from the proximal end to the distal end and terminating at a guide wire exit port.

4. The catheter device of claim 1 further comprising:
   an electrosurgical generator operatively connected to the cutting wire, wherein a dysfunctional sphincter can be ablated by simultaneously contacting the cutting wire and the dysfunctional sphincter and energizing the cutting wire.

5. The catheter device of claim 1, wherein the handles comprises a first portion and a second portion, the second portion being slideable relative to the first portion, the second portion further being connected to the cutting wire, wherein sliding the second portion causes deflection of the distal end.

6. The catheter device of claim 1 further comprising:
an aspiration passageway extending through the elongate sheath and parallel to the longitudinal axis from the proximal end to the distal end and terminating at an aspiration passageway exit port; and
an aspirator operatively connected to the aspiration passageway at the proximal end.

7. The catheter device of claim 1 further comprising:
a plurality of radiopaque markings located on the elongate sheath, the markings being separated by predetermined lengths.

8. The catheter device of claims 1 wherein:
the elongate sheath is made of polytetrafluoroethylene.

9. The catheter device of claim 1 further comprising:
a tapered tip located at a terminal distal end of the elongate sheath.

10. A catheter device for diagnosing a dysfunctional sphincter and ablating the sphincter, comprising:
an elongate sheath comprising a manometry data collecting portion and a sphincter cutting portion;
wherein the elongate sheath further comprises:
a proximal end, a distal end and a longitudinal axis extending therebetween,
a cutting wire passageway extending along the longitudinal axis from the proximal end to the distal end;
a cutting wire extending longitudinally through the cutting wire passageway from the proximal end to the distal end, the cutting wire having an exposed portion extending distally from the distal end of the sheath and along a pathway that is substantially parallel to the longitudinal axis of the sheath; and
a handle operatively connected to the cutting wire wherein a dysfunctional sphincter can be ablated remotely.

11. The catheter device of claim 10 further comprising:
an aspiration passageway extending through the elongate sheath and parallel to the longitudinal axis from the proximal end to the distal end and terminating at an aspiration passageway exit port; and
an aspirator operatively connected to the aspiration passageway at the proximal end.

12. The catheter device of claim 10 further comprising:
a plurality of radiopaque markings located on the elongate sheath, the markings being separated by predetermined lengths.

13. The catheter device of claim 10, wherein the elongate sheath is made of polytetrafluoroethylene.

14. The catheter device of claim 10 wherein:
the cutting wire is selected from the group consisting of a needle knife and an electrosurgical cutter.

15. The catheter device of claim 10, wherein the elongate sheath further comprises:
the distal end further comprising the manometry data collecting portion;
a manometry passageway extending along the longitudinal axis from the proximal end to the manometry data collecting portion, the manometry passageway terminating at the manometry data collecting portion in an exit port;
a pressure transducer operatively connected to the manometry passageway; and
a manometry assembly removably coupled to the manometry passageway at the proximal end, the manometry assembly comprising an infusion pump operatively connected to the manometry passageway, and a data recording unit operatively connected to the pressure transducer,
wherein a tension of the sphincter is determined by measuring the pressure of a column of fluid infused through the manometry passageway.

16. The catheter device of claim 10 further comprising:
a guide wire passageway extending along the longitudinal axis from the proximal end to the distal end and terminating at a guide wire exit port.

17. The catheter device of claim 10 further comprising:
an electrosurgical generator operatively connected to the cutting wire, wherein a dysfunctional sphincter can be ablated by simultaneously contacting the cutting wire and the dysfunctional sphincter and energizing the cutting wire.

18. The catheter device of claim 10 wherein the handle comprises:
a first portion and a second portion, the second portion being slideable relative to the first portion, the second portion further being connected to the cutting wire,
wherein sliding the second portion causes extension or retraction of the cutting wire.

19. A catheter device for diagnosing a dysfunctional sphincter and ablating the sphincter, comprising:
an elongate sheath having a longitudinal axis between a proximal end and a distal end, the distal end having a sphincter cutting portion and a manometry data collecting portion coupled to the sphincter cutting portion;
a passageway extending along the longitudinal axis from the proximal end to the manometry data collecting portion, the passageway terminating at the manometry data collecting portion in an exit port;
a pressure transducer operatively connected to the passageway; and
a manometry assembly removably coupled to the passageway at the proximal end, the manometry assembly comprising an infusion pump operatively connected to the passageway, and a data recording unit operatively connected to the pressure transducer,
wherein a tension of the sphincter is determined by measuring the pressure of a column of fluid infused through the passageway;
a cutting wire passageway extending longitudinally from the proximal end to the sphincter cutting portion, a cutting wire connected to the sphincter cutting portion, the cutting wire extending longitudinally from the sphincter cutting portion through the cutting wire passageway to the proximal end, the cutting wire further having an exposed portion located alongside the sphincter cutting portion,
wherein the cutting wire is adapted for ablating the sphincter; and
a proximal assembly operatively connected to the proximal end, the proximal assembly comprising a handle operatively connected to the proximal end, the handle comprising a first portion and a second portion, the second portion being slideable relative to the first portion, the second portion further being connected to the cutting wire,
wherein the distal end can be aimed in a direction that facilitates cannulating the sphincter, measuring sphincter tension and ablating the sphincter, and an electrosurgical generator operatively connected to the second portion.

20. A catheter device for diagnosing a dysfunctional sphincter and ablating the sphincter, comprising:
an elongate sheath having a longitudinal axis between a proximal end and a distal end, the distal end having a sphincter cutting portion and a manometry data collecting portion coupled to the sphincter cutting portion;
a plurality of manometry passageways extending longitudinally from the proximal end to the manometry data collecting portion, each of the passageways having a first port exiting the passageway at the manometry data collecting portion;

a pressure transducer operatively connected to the manometry passageways;

a manometry assembly removably coupled to the manometry passageways at the proximal end, the manometry assembly comprising an infusion pump operatively connected to the first and second passageways, and a data recording unit operatively connected to the pressure transducer, wherein an accurate reading of sphincter tension can be determined by measuring the pressure of a column of fluid infused through the first and second passageways;

a cutting wire passageway extending longitudinally from the proximal end to the sphincter cutting portion, a cutting wire connected to the sphincter cutting portion, the cutting wire extending longitudinally from the sphincter cutting portion through the cutting wire passageway to the proximal end, the cutting wire further having an exposed portion located alongside the sphincter cutting portion, wherein a dysfunctional sphincter can be ablated;

a tapered tip located on the distal end of the elongate sheath;

a guidewire passageway extending along the longitudinal axis from the proximal end to the tapered tip and having an exit port located at the distal end of the tapered tip;

an aspiration passageway extending along the longitudinal axis, the aspiration passageway having an exit port communicating the passageway with an outside environment wherein excess fluids can be aspirated from the outside environment;

a proximal assembly operatively connected to the proximal end, the proximal assembly comprising a handle operatively connected to the proximal end, the handle comprising a first portion and a second portion, the first portion having a thumb ring, the second portion having two finger rings, the second portion being slideable in relation to the first portion, the second portion further being connected to the cutting wire, wherein the distal end can be aimed in a direction that facilitates cannulating the sphincter, measuring sphincter tension and ablating the sphincter, and an electrosurgical generator operatively connected to the second portion; and a plurality of radiopaque markings fixed to the sheath, the markings being spaced by predetermined lengths.

21. A method of treating a dysfunctional sphincter, comprising the steps of:

providing a catheter device comprising:

an elongate sheath having a longitudinal axis between a proximal end and a distal end, the distal end having a sphincter cutting portion and a manometry data collecting portion; and a proximal assembly operatively connected to the proximal end, the proximal assembly comprising a handle operatively connected to the sphincter cuffing portion and the manometry data collecting portion, and an electrosurgical generator operatively connected to the proximal assembly;

positioning an endoscope having a catheter passageway adjacent to a sphincter opening, the catheter passageway terminating in a catheter passageway exit port;

extending the elongate sheath of the catheter device through the catheter passageway to a position wherein the distal end of the elongate sheath protrudes from the exit port and is adjacent to the sphincter opening;

cannulating the sphincter opening with the distal end of the elongate sheath;

advancing the elongate sheath into the sphincter opening to a position where the manometry data collecting portion aligns with the sphincter;

operating the manometry data collecting portion so as to determine a tension of the sphincter;

positioning the sphincter cutting portion adjacent to the sphincter after operating the manometry data collecting portion; and ablating the sphincter by operating the sphincter cutting portion, thereby treating a portion of the sphincter.

22. A catheter device for diagnosing a dysfunctional sphincter and ablating the sphincter, comprising:

an elongate sheath comprising a manometry data collecting portion and a sphincter cutting portion:

wherein the elongate sheath further comprises:

a proximal end, a distal end and a longitudinal axis extending therebetween the distal end comprising the manometry data collecting portion;

a manometry passageway extending along the longitudinal axis from the proximal end to the manometry data collecting portion, the manometry passageway terminating at the manometry data collecting portion in an exit port, and a pressure transducer operatively connected to the manometry passageway for measuring a pressure of a column of fluid infused through the manometry passageway, wherein the manometry passageway further comprises a plug distal to the exit port.

23. The catheter device of claim 22 further comprising a plurality of manometry passageways, each of the passageways comprising an exit port exiting the passageway at the manometry data collecting portion.

24. The catheter device of claim 22 further comprising a manometry assembly removably coupled to the manometry passageway at the proximal end, the manometry assembly comprising an infusion pump operatively connected to the manometry passageway.

25. The catheter device of claim 22 wherein the sheath further comprises a radiopaque marking at the exit port.

26. A method of treating a dysfunctional sphincter, comprising the steps of:

providing a catheter device comprising:

an elongate sheath having a longitudinal axis between a proximal end and a distal end, the distal end having a sphincter cutting portion and a manometry data collecting portion; and a manometry passageway extending longitudinally from the proximal end to the manometry data collecting portion, the manometry passageway comprising a first port exiting the passageway at the manometry data collecting portion;

providing a pressure transducer operatively connected to the manometry passageway;

advancing the distal end of the sheath so that the manometry data collecting portion is adjacent to a sphincter opening;

measuring a pressure of a column of fluid infused through the manometry passageway and exiting the first port to determine a sphincter tension;

positioning the sphincter cutting portion adjacent to the sphincter; and cutting the sphincter by operating the sphincter cutting portion.

27. The method of claim 26 comprising the step of operating the sphincter cutting portion by sliding movement of a handle to change the position of the sphincter cutting portion with respect to a terminal distal tip.

* * * * *

UNITED STATES PATENT AND TRADEMARK OFFICE
CERTIFICATE OF CORRECTION

| | |
|---|---|
| PATENT NO. | : 7,056,319 B2 |
| APPLICATION NO. | : 10/309681 |
| DATED | : June 6, 2006 |
| INVENTOR(S) | : Giuseppe Aliperti et al. |

It is certified that error appears in the above-identified patent and that said Letters Patent is hereby corrected as shown below:

Column 8, in claim 5, line 1, after "wherein the" delete "handles" and substitute --handle-- in its place.

Signed and Sealed this

Nineteenth Day of December, 2006

JON W. DUDAS
*Director of the United States Patent and Trademark Office*